United States Patent

Myers et al.

[11] Patent Number: 5,512,727
[45] Date of Patent: Apr. 30, 1996

[54] HOT GRIP ASSEMBLY

[75] Inventors: Jeffrey L. Myers, West Chester; Robert W. Aho, Cincinnati; Douglas M. Carper, West Chester; Earl D. Deaton, Cincinnati; Thomas J. Dunyak, West Chester; Ely E. Halila, Cincinnati, all of Ohio

[73] Assignee: General Electric Company, Cincinnati, Ohio

[21] Appl. No.: 216,994

[22] Filed: Mar. 24, 1994

[51] Int. Cl.⁶ .............................. G01N 3/08; G01N 3/18; H05B 3/00
[52] U.S. Cl. .................. 219/201; 374/50; 73/859; 73/860
[58] Field of Search ...................... 219/390, 200, 219/201; 374/49, 50, 47; 73/828, 830, 831, 833, 834, 854, 859, 860, 826, 821, 825, 826, 856, 857

[56] References Cited

U.S. PATENT DOCUMENTS

| | | | |
|---|---|---|---|
| 4,537,080 | 8/1985 | Christiansen | 73/859 |
| 4,652,409 | 3/1987 | Leese et al. | 264/22 |
| 5,188,456 | 2/1993 | Burke et al. | 73/826 |
| 5,202,542 | 4/1993 | Ferguson | 374/50 |
| 5,286,108 | 2/1994 | Whatley et al. | 73/826 |

*Primary Examiner*—Teresa J. Waldberg
*Assistant Examiner*—Raphael Valencia
*Attorney, Agent, or Firm*—Andrew C. Hess; David L. Narciso

[57] ABSTRACT

A gripping system for use in uniaxial testing of test specimens at elevated temperatures, typically above 900°–1000° F. The uniaxial mechanical testing is typically tensile testing conducted on high temperature engineering materials which operate under severe conditions at elevated temperatures. The gripping system includes a gripping element having a first section adapted to contact the test specimen wherein a heater is received in the second section for heating the gripping surface. The heater is designed to heat the gripping surface and the test specimen to the desired temperature.

18 Claims, 4 Drawing Sheets

HOT GRIP ASSEMBLY

BACKGROUND OF THE INVENTION

1. Field of the Invention

This invention relates to wedge type gripping systems for tensile testing and, more particularly, to a gripping element for use in the gripping system for testing materials at elevated temperatures.

2. Description of the Prior Art

The current consensus regarding mechanical tensile/fatigue testing is to utilize a rigid gripping system to provide consistent test specimen alignment from one test to the next. There is also a need to control the gripping forces applied to the tested material so as not to cause it unnecessary damage. During elevated temperature testing, the tested materials change dimensionally prior to and during the test. Dimensional changes occur due to applied mechanical forces and temperature changes. For this reason, the grip pressure also needs to be controlled dynamically to compensate for these dimensional changes.

Commercially available hydraulic activated grips exist but are not designed for operation at high temperatures (in excess of 1000° F.) during the gripping operation. The high test temperatures are required to test the newer generation materials such as high temperature composite matrices at temperatures as high as 3000° F. This precludes making gripping materials and grips themselves of material sufficient to survive these extreme temperatures. Most hydraulically activated grips are designed to operate at or near room temperature and this limitation creates problems when conducting long term testing on materials at elevated temperatures that exhibit oxidation damage mechanisms. One such grip is the MTS647 Hydraulic Wedge Grip. As a result, the current approach to elevated tensile and fatigue testing incorporates a "cold grip configuration" where the center of the specimen is heated and the grip region is outside the hot environment. This test configuration presents several potential problems: (1) large thermal gradients and thermal stresses are produced in the specimen which contributes to failure; (2) materials which exhibit an increased strength at elevated temperatures fail outside the test environment region and at the grips; and (3) protective environmental coatings which tend to work over a limited temperature range do not protect the entire specimen between the hot section of the cold grips. This produces failures outside the test environment region.

To overcome these problems, it has become necessary to increase the temperature of the tested material within the grip region, such as a modified wedge that extends outside the grip body to allow for heating of the wedge itself by either surrounding the extended wedge segment with resistant heating coils or with an inductive heating coil. However, the following problems exist with this arrangement. (1) Acceptable thermal profiles on the test specimen are impossible to achieve due to the tremendous heat flow from the wedges into the grip body and/or cooling water; (2) applying gripping forces by means of an unconstrained wedge becomes extremely difficult to achieve structurally, particularly at elevated temperatures; (3) by extending the wedge beyond the confines of the grip body, wedge material is subjected to a complex, stress state of bending, compression, tension and shear forces that will be further debilitating when operated at elevated temperatures; (4) current art does not provide heat insulating materials to combat heat transfer from the heated wedge area into the grip body, thus requiring an increase in unneeded amounts of heat energy to compensate for losses into the grip body and accordingly, increase the grip body temperature and the cooling capacity needs of the grip body; (5) extending the wedge beyond the grip body will require a longer load train; and (6) if the heating of the wedges are to be accomplished using radio frequency (RF) induction energy then it will require the use of two expensive RF generators and the additional utilities needed to support and operate them.

Accordingly, it is an object of the present invention to provide a wedge for a grip that is capable of being heated and overcomes the prior art problems.

SUMMARY OF THE INVENTION

The present invention is an improved gripping system for use in uniaxial testing of test specimens at elevated temperatures, typically above 900°–1000° F. The uniaxial mechanical testing is typically tensile testing conducted on high temperature engineering materials which operate under severe conditions at elevated temperatures. The gripping system of the present invention includes a gripping element comprising a first section adapted to contact the test specimen wherein a heater is received in the second section for heating the gripping surface. The heater is designed to heat the gripping surface and the test specimen to the desired temperature. The heater includes means to maintain the gripping surface and the test specimen held by the gripping surface at the predetermined temperature required for the elevated mechanical test. The system of the present invention enables the test specimen to be properly gripped to ensure application of the required loads during testing while also having the temperature reliably maintained at the desired temperature.

Because the gripping element includes a heater to heat the specimen, it is desirable to include in the first section of the gripping element means for cooling the gripping element to carry away excess heat. This may be in the form of cooling water having an inlet which is circulated through the first section before it is discharged through an outlet. Cooling the gripping element will prevent the grip, which houses the heater, from overheating.

Other features and advantages of the present invention will be apparent from the following more detailed description of the preferred embodiments, taken in conjunction with the accompanying drawings which illustrate, by way of example, the principles of the invention.

DESCRIPTION OF THE PREFERRED EMBODIMENTS

Figure 1:
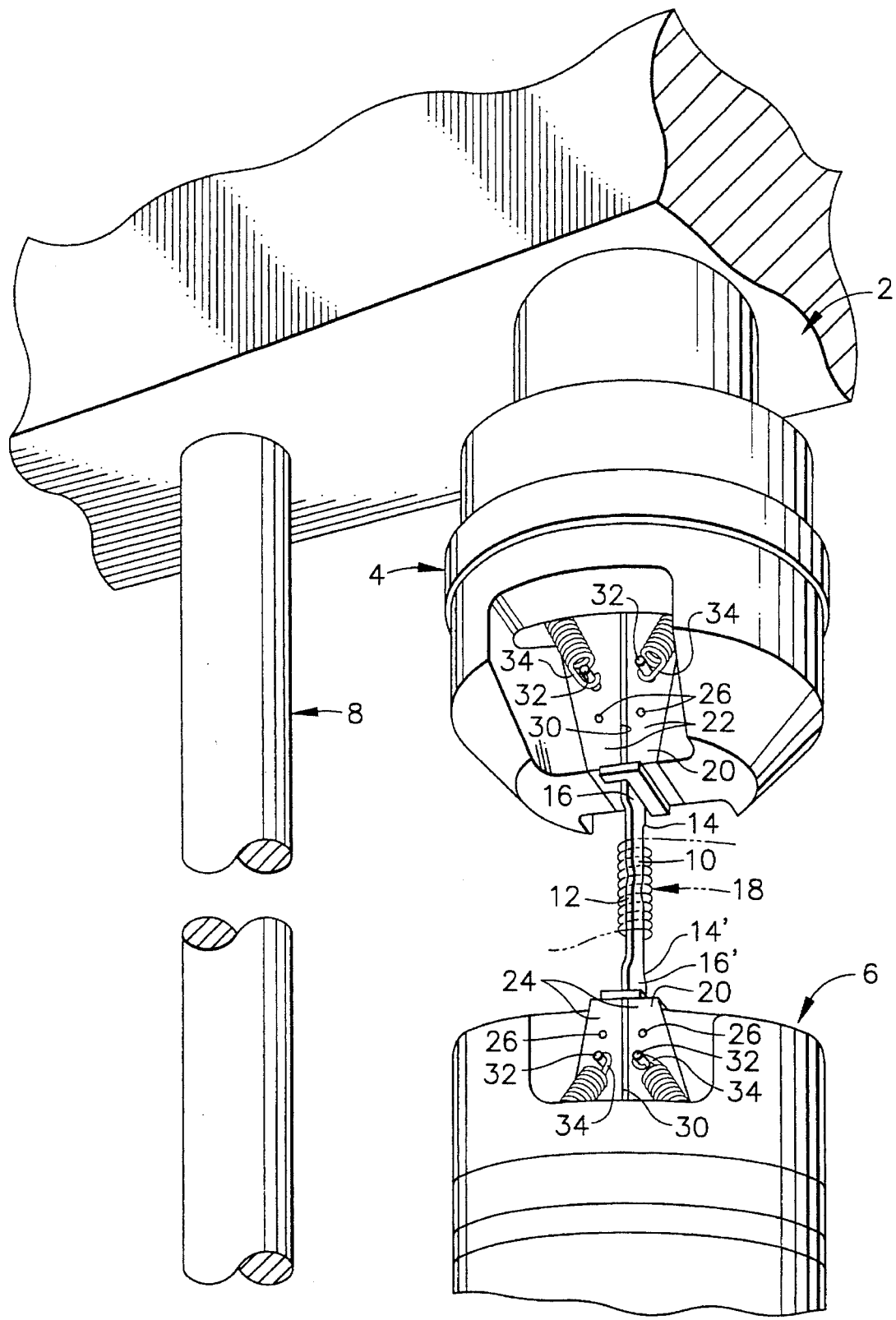
FIG. 1 is a plan view of a prior art tensile testing machine with prior art grips.

FIG. 1 shows a prior art tensile testing machine 2, such as a MTS Systems Corporation with 647 Hydraulic Wedge Grip. The tensile testing machine 2 includes a first hydraulic wedge grip 4 positioned above a second hydraulic wedge grip 6. The first grip 4 is attached to frame 8, and the second grip 6 is attached to the hydraulic activator (not shown), whereby when the hydraulic actuator is actuated the second wedge grip 6 moves away from the first wedge grip 4.

A test specimen 10 can be received in between the wedges of the first wedge grip 4 and the second wedge grip 6 so as to hold the test specimen 10 along a longitudinal axis that passes through the test specimen 10. The test specimen includes an ungripped gauge section 12, which increases in cross-sectional area to shoulder areas 14 and 14', and grip areas 16 and 16'. Grip area 16 is adapted to be received by the first wedge grip 4 and a grip area 16' is adapted to be received by the second wedge grip 6. Test specimen 10 can be a ceramic matrix composite or other "high temperature" material system. In this case, as stated earlier, the testing should be conducted at elevated temperatures on the order of as high as 3000° F. A conventional heating device 18, shown in phantom in FIG. 1, is wrapped around the gauge section 12 so as to increase the test specimen temperature in that area.

Gripping elements 20 are adapted to be received by both the first wedge grip 4 and second wedge grip 6 so as to hold the grip areas 16 and 16' in place. Specifically, the first wedge grip 4 receives a pair of gripping elements 22 and second wedge grip 6 receives a pair of gripping elements 24. Each gripping element contains a water cooling part 26 so as to keep the gripping elements cooled. Each of the elements also includes a gripping surface 30 and spring retaining member 32 that receives a spring clip 34 to hold each pair of elements 22 and 24 together. The gripping surface 30 is preferably a roughened surface so that when the gripping areas 16 and 16' of the test specimen 10 is received by the pair of gripping elements 22 and 24, the respective gripping surfaces 30 are adapted to hold the test specimen in place.

Figure 2:
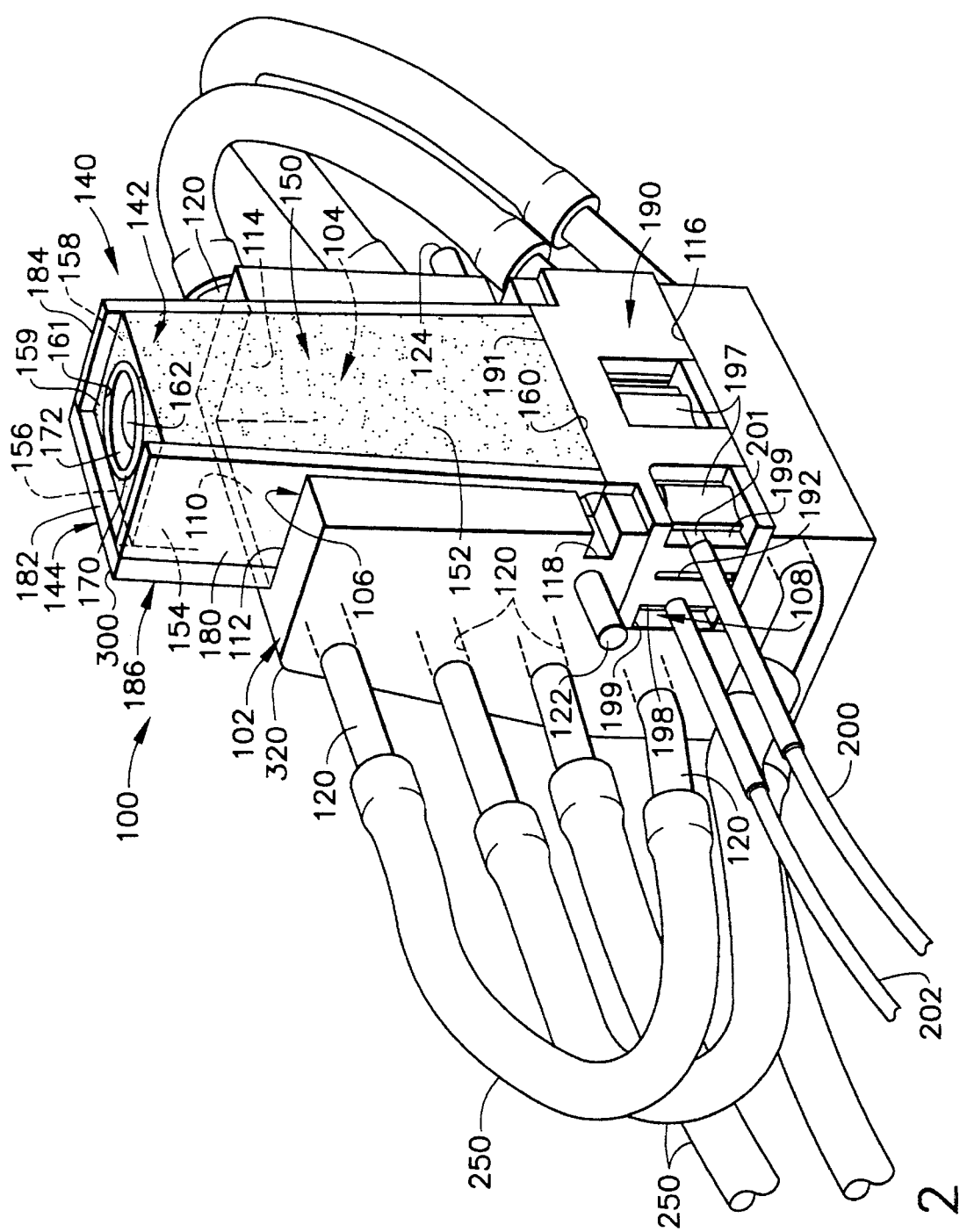
FIG. 2 is a perspective plan view of an assembled heated gripping wedge element made in accordance with the present invention.

Referring now to FIG. 2, our invention is a gripping wedge element 100 of a hot grip assembly that is made to replace each of the gripping elements 22 and 24 of the present tensile testing machine 2. The element 100 includes a first section or body 102 made of tool steel. The outer profile of the body 102 is similar to that of the outer profile of the gripping element 20. The body 102 includes a recess 104 having a first part 106 and a second part 108. The recess 104 is defined by inner surfaces of a back wall 110, side wall 112, side wall 114, wherein side walls 112 and 114 depend from back wall 110, and a base wall 116 attaches to back wall 110, side walls 112 and 114. A thermocouple slot 118 is provided in side wall 112. Cooling parts 120 are provided inside back wall 110 and base wall 116. The cooling parts 120 are adapted to receive water from a cooling source so that the cooling water will flow through the parts 120. A retaining ring 122 is provided on wall 112 and a retaining ring 124 is provided on wall 114. Retaining rings 122 and 124 are adapted to receive springs 34 in the same manner as the current type grip elements 22 and 24.

Figure 4:
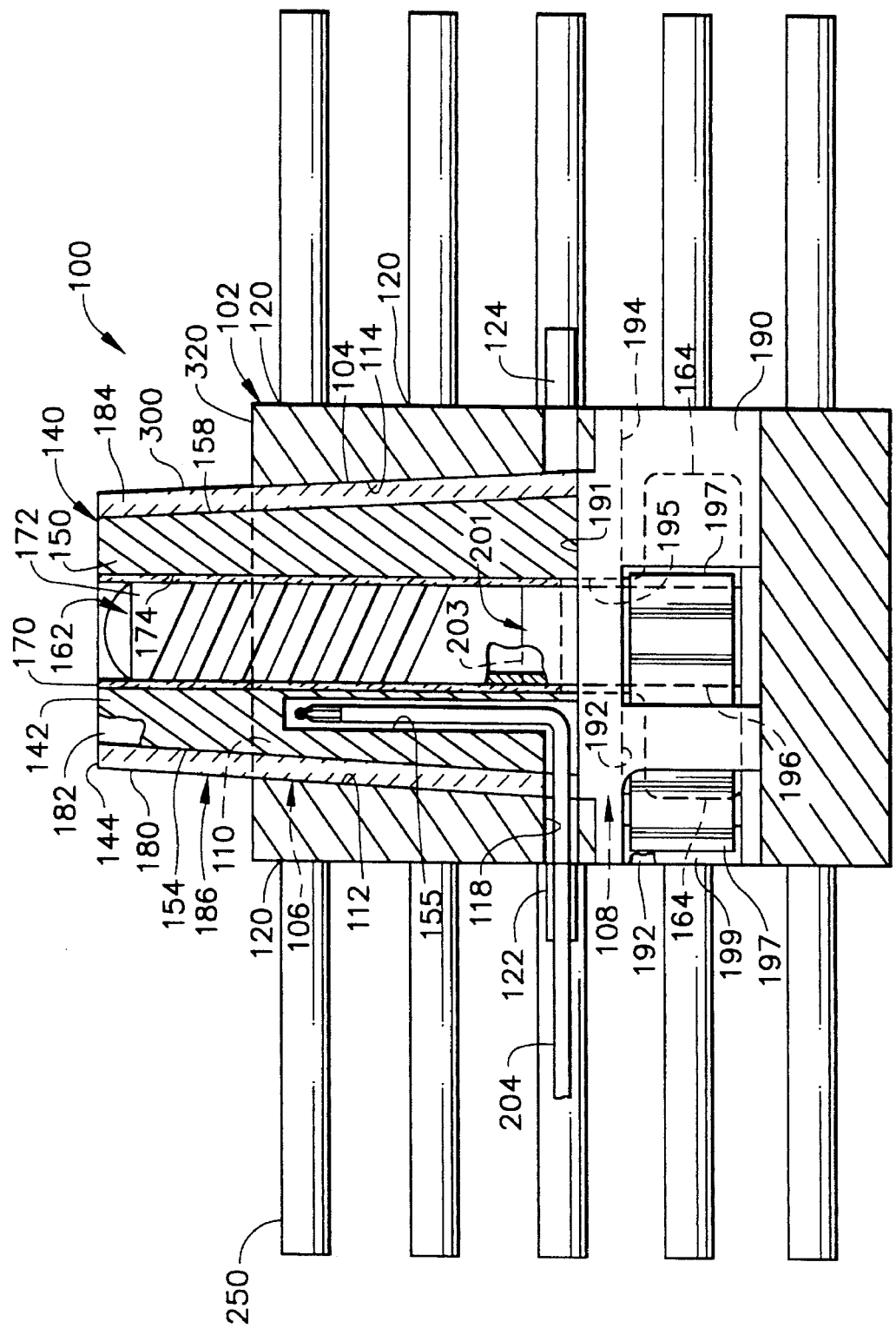
FIG. 4 is a front view of a portion of the heated grip assembly.

A heating assembly or second section 140 is adapted to be received by recess 104. The heating assembly 140 includes a heating section 142 and an insulating section 144. The heating section 142 includes a wedge insert 150. Preferably, the insert 150 is made up of a high temperature oxidation resistant alloy such as Hastalloy X or Waspalloy. The wedge insert 150 includes a trapezoidal shaped front gripping surface 152, a first side surface 154 through which a thermocouple tunnel 155 is provided as shown in FIG. 4, back surface 156, a second side surface 158, an upper surface 159 and lower surface 160. A cylindrical slot 161 passes through the wedge 150 from the upper surface 159 to the lower surface 160. Preferably, the gripping surface 152 is weld sputtered, which is well known in the art, and is trapezoidal in shape.

As shown in FIG. 4, a heating element 162 is adapted to be received by the slot 161. The heating element 162 can be a 115 VAC, 3-4 amp, silicon carbide heating element, which is substantially cylindrical in shape and formed into double helix shape. One such heating element is an ignition starter element used for natural gas ovens and manufactured by the Carborundum Corporation, Model No. WI4X444. Insulating tabs 164 depend from the heating element 162. An electrically insulated ring 170 preferably made of mullite and is received by an upper end 172 of the cylindrical portion of the heating element 162 and positioned between the heating element 162 and a cylindrical surface 174 that defines the cylindrical slot 161 of the wedge 150. The insulating ring 170 prevents the possibility of an electrical short occurring by the heating element 162 contacting the wedge 150.

The insulating section 144 includes a heat dam wall 180, a heat dam wall 182 and a heat dam wall 184 adjacent to surface 154, surface 156 and surface 158 of wedge 150, respectively. Further, the heat dam walls 180, 182 and 184 form a heat dam structure 186. Heat dam structure 186 is received by the first part 106 of recess 104 and positioned between surfaces 154, 156 and 158 and walls 110, 112 and 114 of the body 102. Preferably, the heat dam structure 186 is made of a zirconia based ceramic, which is both an electrical insulator and a heating insulator.

Figure 3:
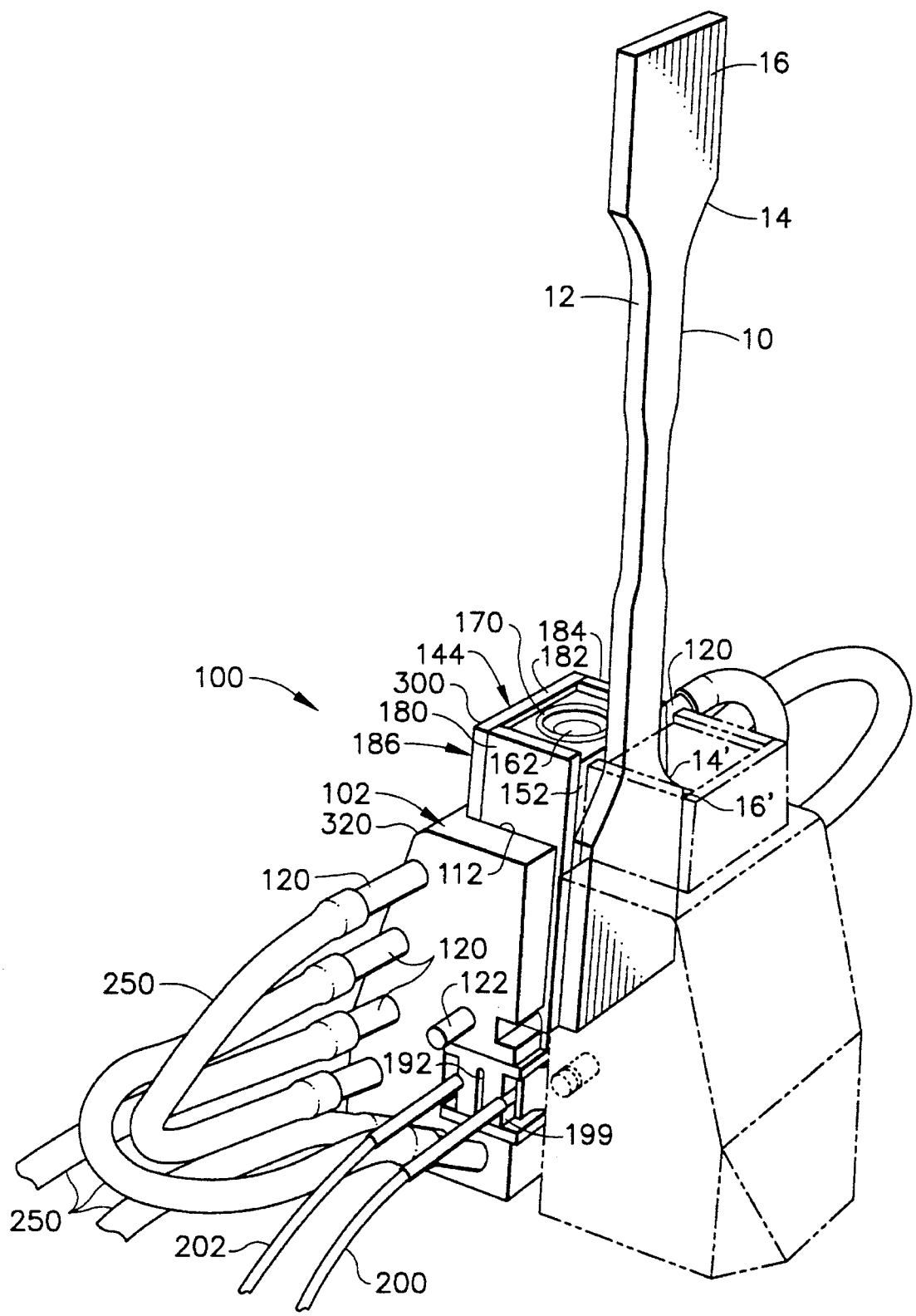
FIG. 3 is a perspective plan view of the heated grip assembly in an assembled arrangement gripping an end of a test specimen.

The second part 108 of recess 104 receives a terminal block 190. Terminal block 190 preferably is made of the same zirconia based ceramic as that of the heat dam structure 186. The lower surface 160 of the wedge 150 rests on an upper surface 191 of the terminal block 190. Accordingly, the insulating section 144, is positioned between the heating section 142 and the body 102. Slots 192 and 194 are provided in and pass through the terminal block 190 and are adapted to receive tabs 164 of the heating element 162. An open topped cylindrical hole 195 passes through the upper surface 191 of the terminal block 190 and receives a cylindrical bottom portion 196 of the heating element 162. Spring contact members or electrical coupling members 197 and 198 (see FIG. 2) are attached to the terminal block 190 through cutouts 199 provided in the terminal block 190 adjacent opposite sides of the bottom portion 196 of heating element 162 and adjacent opposite contacts of the heating element 162. Electrical lead 200 is adapted to be received by the terminal block 190 and held in place by spring contact 197 so that lead 200 is urged by spring contact 197 to touch contact 201 of the heater element 162. Likewise, an electrical lead 202 (see FIGS. 2 and 3) is adapted to be received by the terminal block 190 and held in place by spring contact 198 (see FIG. 2) so that lead 202 (see FIGS. 2 and 3) is urged by spring contact 198 to touch contact 203 of the heater element 162. A thermocouple or temperature sensor 204 is received by the thermocouple slots 118 and 155 and positioned adjacent the wedge 150.

In operation, the two pairs of gripping wedge elements 100 are received by grips 4 and 6 in a similar manner as the prior art gripping elements so that the bodies 102 contact grips 4 and 6. Since the outer profile of body 102 is the same as that of wedge elements 22 and 24 grips 4 and 6 need not be modified to accept the grip assemblies 100. The heating device 18 is positioned around the gauge section 12 and the respective gripping surfaces 152 face each other and receive respective areas 16 and 16' of the test specimen 10. Cooling lines 250 are received by the cooling ports 120 so that cooling water can pass through the body 102. Preferably, the cooling lines 250 are made of flexible plastic tubing. The thermocouple 204, which is positioned within the thermocouple slots 118 and 155, is connected to a temperature measuring device, which is well known in the art. Electrical leads 200 and 202 are received by appropriate spring contacts 197 and 198 so that an electrical circuit is formed by the leads 200 and 202 and the heater element 162 via contacts 201 and 203. Preferably, upper portions of the heating assembly 140 extend above an upper portion 320 of the body 102 so that the upper portions 300 can be positioned in close proximity to the heating device 18 and minimize thermal stresses in the test specimens 10.

The grips 4 and 6 are then hydraulically actuated by hydraulic actuator so that they move away from one another along a longitudinal Z axis, thereby forcing the surfaces 152 against respective gripping areas 16 and 16' so as to apply a longitudinal force or tensile force against test specimen 10. This is caused by a wedged outer profile about the Z plane of body 102 coacting with a complementary wedged profile of the respective grips and thereby causing surfaces 152 to frictionally hold areas 16 and 16' in place. A similar complementary wedging profile about the Y-Z plane is provided between an outer surface of the dam structure 186 and recess 104 of body 102, and an inner surface of the dam structure 186 and side surfaces 154 and 158 of heating section 142. Accordingly, as the specimen 10 is elongated in the longitudinal direction and a longitudinal force in the Z direction is applied to the gripping surface 152 and in turn to heating section 142. The heat assembly 140 is held in place onto the body 102 by a wedging effect by coacting surfaces of the body 102, the dam structure 186 and the heating section 142. The heating device 18 is activated so as to heat the gauge section 12 to an appropriate test temperature. Likewise, the electrical current passes through each lead 200 and 202 and then turn through the respective heating element 162. Each heating element 162 via electrical resistance increases in temperature. The increased temperature from the heating element 162 pass through the wedge 150 and into the grip areas 16 and 16'. The heat dam structure 186 and terminal block 190 act as heat insulators to insulate the body 102 from the heated section 142. Cooling water passes through cooling lines 250 and cooling parts 120 thereby cooling body 102. The thermocouple 204 can also be electrically coupled to a signal conditioner and temperature controller that controls the amount of current passing through heating element 162 and in turn, the temperature of the gripping surface 152 so that the temperature of the gripping surface 152 is substantially the same as the temperature of the heated gauge section 12. Hence, the temperature of the entire test specimen 10 can be accurately and easily controlled, thereby avoiding the problems of the prior art as discussed above.

Having described the presently preferred embodiment of our invention, it is to be understood that it may otherwise be embodied within the scope of the appended claims.

We claim:

1. A gripping element for use with a hydraulic wedge gripping machine for uniaxial mechanical testing a test specimen at elevated temperatures and having means for receiving said gripping element, said gripping element comprising a first section adapted to contact the gripping machine, said first section having a passageway adapted to receive a cooling fluid, and a second section having a gripping surface adapted to contact the test specimen wherein a heater is received in said second section for heating the gripping surface.

2. A gripping element as claimed in claim 1 wherein said heater includes an electrical heating element.

3. A gripping element as claimed in claim 2 wherein said heating element is made of silicon carbide.

4. A gripping element as claimed in claim 3 wherein said heating element is a cylindrically shaped double helix.

5. A gripping element as claimed in claim 1 further comprising a third section positioned between said first section and said second section, said third section formed from an insulating material.

6. A gripping element as claimed in claim 5 wherein said third section is made of a zirconia based ceramic material.

7. A gripping element as claimed in claim 1 wherein said second section is made of a high temperature oxidation resistant material.

8. A gripping element of claim 1 wherein said first section is made of hardened steel.

9. A gripping element of claim 1 further comprising a temperature sensor contained within said second section.

10. A gripping element of claim 9 wherein said temperature sensor is a thermocouple.

11. A gripping element of claim 1 further comprising an electrical coupling member attached to said second section adapted to electrically couple said heater to a closed loop controlled power source.

12. A gripping element of claim 11 wherein said electrical coupling member is a spring contact.

13. A gripping element of claim 1 wherein said first section includes a back wall having an inner surface, two depending side walls each having an inner surface attached to said back wall and a base wall having an inner surface depending from said side walls and said back wall wherein, a recess is defined by said back wall inner surface, said side wall inner surfaces and said base wall inner surfaces, and said second section is received by said recess.

14. A gripping element of claim 13 wherein said second section includes a heated section having an upper surface, a lower surface, a front surface, a first side surface, a rear surface, and a second side surface, wherein said front surface is roughened and adapted to frictionally grip a test specimen and said first side surface, said back surface, said second side surface and said lower surface are received with said recess defined in said first section, said heated section further including a recess adapted to receive said heater.

15. A gripping element as claimed in claim 14 wherein said second section further includes an insulating section comprising insulation positioned in said recess of said first section and between said first section and said heated section.

16. A gripping element as claimed in claim 15 wherein said first section is adapted to wedgedly coact with said second section so that said first section is held in place while the heated section expands and contracts without damaging said first section and said second section.

17. A uniaxial mechanical testing machine comprising:

a frame;

a first wedge grip mounted to said frame and a second wedge grip, said first grip and said second grip adapted to hold and elongate a test specimen along a longitudinal axis which passes through the test specimen; each of said grips having a recess and adapted to receive a pair of gripping wedge shaped elements;

each of said gripping wedge shaped elements comprising:

a first wedge shaped section having a passageway adapted to receive a cooling fluid, and adapted to contact a respective grip and a second section having a gripping surface adapted to contact the test specimen wherein a heater is received in said second section for heating the gripping surface, so that a gripping surface of one of said pair of element faces a gripping surface of the other of said pair of said gripping elements and an end of the test specimen is adapted to be sandwiched under clamping pressure between and frictionally held in place by said respective gripping surfaces; and means for moving said first grip in relation to said second grip along the longitudinal axis.

18. A gripping element of claim 17 wherein said first section includes a back wall having an inner surface, two depending side walls each having an inner surface attached to said back wall and a base wall having an inner surface depending from said side walls and said back wall that form a recess which receives said second section.

* * * * *